United States Patent [19]
Ye et al.

[11] Patent Number: 5,646,027
[45] Date of Patent: Jul. 8, 1997

[54] PROCESS FOR THE PRODUCTION OF GELATINASE CATALYTIC DOMAIN PROTEIN

[75] Inventors: Qi-Zhuang Ye; Linda Lea Johnson; Donald John Hupe, all of Ann Arbor, Mich.

[73] Assignee: Warner-Lambert Company, Morris Plains, N.J.

[21] Appl. No.: 303,270

[22] Filed: Sep. 8, 1994

[51] Int. Cl.$^6$ .................. C12N 15/57; C12N 15/63; C12P 21/00
[52] U.S. Cl. .............. 435/219; 435/212; 435/320.1; 536/23.2
[58] Field of Search ................... 435/219, 226, 435/320.1, 212; 536/23.2

[56] References Cited

U.S. PATENT DOCUMENTS 4,923,818  5/1990  Goldberg et al. ............... 435/226

OTHER PUBLICATIONS

Wilhelm et al., J. Biol. Chem. 264:17213–17221 (1989).
Huhtala et al., J. Biol. Chem. 266:16485–16490 (1991).
Tezuka et al., J. Biol. Chem. 269:15006–15009 (1994).
Murphy et al., Biochem. J. 283:637–641 (1992).
Ye et al., Biochemistry 31:11231–11235 (1992).
Banyai et al., Biochem J. 298:403–407 (1994).
Murphy et al., J. Biol. Chem. 269:6632 (1994).
Pourmotabbed, Ann. N.Y. Acad. Sci. 732:372–374 (1994).

Primary Examiner—Charles L. Patterson, Jr.
Assistant Examiner—Eric Grimes
Attorney, Agent, or Firm—Francis J. Tinney

[57] ABSTRACT

A process for the production of the catalytic domain, without propeptide, C-terminal domain, and the fibronectin-like insert, of human gelatinases is described which comprises culturing transformed E. coli host cells carrying a synthetic DNA sequence encoding the catalytic domain as well as a method for screening for inhibitors of a gelatinase; a method for determining the 3-dimensional structure of the catalytic domain of a gelatinase; and pharmaceutical compositions of human gelatinase catalytic domain protein which are useful in treating herniated vertebral discs, dermal ulcers, modifying scar tissue formation, and joint diseases.

6 Claims, 10 Drawing Sheets

```
                -3        10         20         30         40
        GCD     MASYNFFPPRKPKWDKNQITYRIIGYTPDLDPETVDDAFARAFQVWSDVT
                   ::  :::: :     ::::::       ::    :   ::   ::
        SCD              FRTFPGIPKWRKTHLTYRIVNYTPDLPKDAVDSAVEKALKVWEEVT
                                   10         20         30         40
                                    SSSSSSSS              HHHHHHHHHHHHHH 50         60         70         80         90
                PLRFSRIHDGEADIMINFGRWEHGDGYPFDGKDGLLAHAFAPGT
                 :: :::  ::::::::  ::   :::::  :  :::: :::
                PLTFSRLYEGEADIMISFAVREHGDFYPFDGPGNVLAHAYAPGP
                  50         60         70         80         90
                   SSSSSSS     SSSSSSS           :::  ::::   SSSSS
```

FIG. 1

```
                    100           110           120           130
GCD    GVGGDSHFDDELWGFCPDQGYSLFLVAAHEFGHAMGLEHSQDPG
       :: :::::: :   :   : :::::::::: ::  :     :
SCD    GINGDAHFDDDEQWTKDTT-GTNLFLVAAHEIGHSLGLFHSANTE
                    100           110           120           130
              SSSSSSSSS                      HHHHHHHHHHHHH 140           150            160           170
       ALMAPIYTYTK---NFRLSQDDIKGIQELYGASPDI
       ::: : :      ::::::::  :::  :   ::
       ALMYPLYHSLTDLTRFRLSQDDINGIQSLYGPPPDSPETP
              140           150            160           170
                                 HHHHHHHHHHH
```

FIG. 1A

```
         10         20         30         40         50         60
AACGAAAGTGCTAGCTACAACTTCTTCCCGCGTAAACCGAAGTGGGACAAAAACCAGATC
                  AlaSerTyrAsnPhePheProArgLysProLysTrpAspLysAsnGlnIle
                  NheI 70         80         90        100        110        120
ACTTACCGTATCATCGGTTACACCCCGGATCCGGAAACTGTAGACATCTGACATCTGCTACGTAAG
ThrTyrArgIleIleGlyTyrThrProAspLeuAspProGluThrValAspAspAlaPhe
                              BamHI 130        140        150        160        170        180
GCACGTGCATTCCAGGTGTGGTCTGACGTTACTCCGCTGCGTTTCTCGCCATCCATGAC
AlaArgAlaPheGlnValTrpSerAspValThrProLeuArgPheSerArgIleHisAsp
PmlI
```

FIG. 2

```
        190              200              210              220              230              240
GGTGAAGCAGACATCATGATAAACTTCGGTCGTTGGGAACATGGTGACGGCTACCCGTTT
CCACTTCGTCTGTAGTACTATTTGAAGCAACCCTTGTACCACTGCCGATGGGCAAA
GlyGluAlaAspIleMetIleAsnPheGlyArgTrpGluHisGlyAspGlyTyrProPhe
                        BspHI 250              260              270              280              290              300
GATGGTAAAGACGGTCTGCTGGCACATGCCCTTCGCTCCGGGTACCGGTGTTGGTGAC
CTACCATTTCTGCCAGACGACCGTGTACGGGAAGCGAGGCCCATGGCCACAACCACTG
AspGlyLysAspGlyLeuLeuAlaHisAlaPheAlaProGlyThrGlyValGlyGlyAsp
                                              KpnI 310              320              330              340              350              360
TCTCACTTCGACGATGATGAGCTGTGGGGTTTCTGCCCGGATCAGGCTACTCTCTGTTC
AGAGTGAAGCTGCTACTACTCGACACCCCAAAGACGGGCCTAGTCCGATGAGAGACAAG
SerHisPheAspAspAspGluLeuTrpGlyPheCysProAspGlnGlyTyrSerLeuPhe
```

FIG. 2A

```
       370        380        390        400        410        420
CTGGTAGCTGCTCACGAATTCGGTCATGCTATGGGTCTGGAGCACTCCCAGGACCCGGGT
GACCATCGACGAGTGCTTAAGCCAGTACGATACCCAGACCTCGTGAGGGTCCTGGGCCCA
 Leu Val Ala Ala His Glu Phe Gly His Ala Met Gly Leu Glu His Ser Gln Asp Pro Gly
                    EcoRI                                      SmaI 430        440        450        460        470        480
GCTCTGATGGCTCCGATATACACCTATAAAAACTTTCGTCTGTCCCAGGACGATATC
CGAGACTACCGAGGCTATATGTGGATATTTTTGAAAGCAGACAGGGTCCTGCTATAG
 Ala Leu Met Ala Pro Ile Tyr Thr Tyr Thr Lys Asn Phe Arg Leu Ser Gln Asp Ile
                                                              EcoRV 490        500        510        520        530
AAAGGTATACAGGAACTGTACGGTGCTTCTCCGGACATCTAAGCTTGAACAATGCA
TTTCCATATGTCCTTGACATGCCACGAAGAGGCCTGTAGATTCGAACTTGTTACGT
 Lys Gly Ile Gln Glu Leu Tyr Gly Ala Ser Pro Asp Ile Ter
                                                HindIII
```

FIG. 2B

PROCESS FOR THE PRODUCTION OF GELATINASE CATALYTIC DOMAIN PROTEIN

BACKGROUND OF THE INVENTION

The present invention relates to a process for the production of a mammalian gelatinase catalytic domain protein, to a synthetic gene expressing the gelatinase catalytic domain, to a purified mammalian gelatinase catalytic domain protein, to pharmaceutical compositions which include the mammalian gelatinase catalytic domain protein and a pharmaceutically acceptable carrier, and to pharmaceutical methods of treatment.

Gelatinases participate in connective tissue remodeling (Woessner J. F., FASEB J., 1991;5:2145–2154) by degrading protein substrates like denatured collagens (gelatins), Type IV collagen (Morel F., et al., Biochem. Biophys. Res. Commun., 1993;191:269–274), and elastin (Senior R. M., et al., J. Biol. Chem., 1991;266:7870–7875). Together with other members in the matrix metalloproteinase family, gelatinases have been implicated in several pathological processes involving connective tissue degradation, such as cancer cell invasion and metastasis (Stetler-Stevenson W., et al., FASEB J., 1993;7:1434–1441).

The potential utility of matrix metalloproteinase inhibitors in controlling these pathological processes has stimulated structure-function studies for this family of zinc-containing enzymes. All matrix metalloproteinases have a signal peptide for secretion, a propeptide containing a cysteine as zinc ligand for maintaining enzyme latency (Van Wart H. E., et al., Proc. Natl. Acad. Sci. USA, 1990;87:5578–5582), and a catalytic domain containing three histidines as zinc ligands for enzymatic activity. Collagenases, stromelysins, and gelatinases have a hemopexin-like C-terminal domain, while matrilysin lacks such domain. Studies with C-terminally truncated stromelysin (Ye Q. -Z., et al., Biochemistry, 1992;31:11231–11235; Marcy A. I., et al., Biochemistry, 1991;30:6476–6483; copending U.S. patent application Ser. No. 08/281,313, filed Jul. 27, 1994, which is a continuation application of U.S. patent application Ser. No. 08/012,705 filed Feb. 3, 1993, discloses a process for the production of the catalytic domain, without propeptide, of human stromelysin), collagenase (Schnierer S., et al., Biochem. Biophys. Res. Commun., 1993;191:319–326) and gelatinase (Murphy G., et al., Biochem. J., 1992;283:637–641) have shown that the catalytic domain is sufficient for peptidase and proteinase activity. However, the C-terminal domain is required for collagenase to degrade helical collagens (Schnierer S., et al., Biochem. Biophys. Res. Commun., 1993;191:319–326; Sanchez-Lopez R., et al., J. Biol. Chem., 1993;268:7238–7247; Hirose T., et al., Proc. Natl. Acad. Sci. USA, 1993;90:2569–2573), and it is involved in binding with TIMPs (Murphy G., et al., Biochem. J., 1992;283:637–641; Baragi V., et al., J. Biol. Chem., 1994;269:12692–12697; Fridman R., et al., J. Biol. Chem., 1992;267:15398–15405) Both 72 kDa and 92 kDa gelatinases have an insert (about 174 amino acid residues) at the catalytic domain, which is homologous to the Type II domain in fibronectin and has the ability to bind gelatin (Collier I. E., et al., J. Biol. Chem., 1992;267:6776–6781; Banyai L., et al., Biochem. J., 1994;298:403–407). The 92 kDa gelatinase has an extra collagen-like insert between the catalytic domain and the C-terminal domain.

The C-terminally truncated gelatinase generated by Murphy et al. (Murphy G., et al., Biochem. J., 1992;283:637–641) contained the 19 kDa fibronectin-like insert and had activity similar to the full length gelatinase against peptide and protein substrates. Recently, Murphy, et al., (Murphy G., et al., J. Biol. Chem., 1994;269:6632–6636) also constructed a mutant of the full length 72 kDa gelatinase with deletion of the fibronectin-like insert, and the deletion mutant had a similar activity in degrading a fluorogenic peptide but a reduced activity against gelatin and casein. With deletion of the fibronectin-like insert, the catalytic domain of gelatinase is homologous to that of other matrix metalloproteinases (Murphy G. J. P., et al., FEBS Lett., 1991;289:4–7). We reconstructed the catalytic domain of human 72 kDa gelatinase (GCD) by connecting the two peptide fragments for the catalytic domain with deletion of the insert (Seq ID No: 1) (FIG. 1). The present GCD lacks both the C-terminal hemopexin-like domain and the fibronectin-like insert. We demonstrate here that the reconstructed 19 kDa GCD expressed in E. coli from a synthetic gene is a competent peptidase and proteinase.

The object of the present invention is the expression, purification, and characterization of a 19 kDa gelatinase catalytic domain (GCD) protein lacking the propeptide, the C-terminal fragment and the fibronectin-like insert (Seq ID No: 1) (FIG. 1). The removal of the propeptide eliminates the need for proteolytic or chemical activation, the removal of the C-terminal fragment removes autolytic sites, thereby making the protein resistant to autodegradation, and the removal of the fibronectin insert (19 kDa) reduces the protein size of the catalytic domain to 19 kDa. The active and stable protein with a mass of 19 kDa is suitable for structure determination by nuclear magnetic resonance spectroscopy and X-ray crystallography, as well as mechanistic studies of catalysis and inhibition. Additionally, the protein is useful in the therapy of various disease states.

SUMMARY OF THE INVENTION

Accordingly, the present invention is directed to a process for the production of the catalytic domain, without propeptide, C-terminal domain, and the fibronectin-like insert, of human gelatinases including both 72 kDa gelatinase and 92 kDa gelatinase, comprising culturing transformed E. coli host cells carrying a DNA sequence encoding the catalytic domain.

In a preferred embodiment of the first aspect of the invention, an E. coli host cell transformed with a replicable expression vector under the control of a promoter such as, for example, a bacterial phage T7 promoter, or a non-T7 promoter, such as, for example, T3, SP6, tac, trc, trp, lac, lambda-$P_L$, and lambda-$P_R$, and the like, expresses a recombinant catalytic domain protein.

In a more preferred embodiment of the first aspect of the invention, the E. coli host cell comprises E. coli strains having T7 RNA polymerase gene either on their chromosome or on a plasmid.

In a most preferred embodiment of the first aspect of the invention, the E. coli strain is BL21(DE3)/pLysS; the expression vector is pGEMEX-GCD wherein the synthetic gene has the sequence specified in FIGS. 2, 2a and 2b (Seq ID No: 3); the catalytic domain protein is human gelatinase catalytic domain protein having the sequence specified in FIGS. 1 and 12 (Seq ID No: 1); and the expression of human gelatinase catalytic domain protein is under the control of bacterial phage T7 promoters.

In a second aspect, the present invention consists of a plasmid pGEMEX-GCD capable of expressing gelatinase catalytic domain protein which is constructed by inserting a synthetic DNA fragment encoding for the protein into plasmid pGEMEX-1.

In a third aspect, the present invention consists of a purified human gelatinase catalytic domain protein having the sequence specified in FIGS. 1 and 12 (Seq ID No: 1).

In a fourth aspect, the present invention consists of a synthetic gelatinase catalytic domain gene having the sequence specified in FIGS. 2, 2a and 2b (Seq ID No: 3).

In a fifth aspect, the present invention consists of a method for determining the ability of a candidate substance to inhibit a gelatinase comprising the steps of:

(a) obtaining a gelatinase catalytic domain protein;

(b) admixing a candidate substance with the protein; and (c) determining the ability of the protein to cleave a substrate in the presence of the candidate substance.

In a preferred embodiment of the fifth aspect of the invention, the gelatinase catalytic domain protein is human gelatinase catalytic domain protein and the substrate is selected from the group consisting of gelatins, thiopeptolide, and fluorogenic peptides.

In a sixth aspect, the present invention consists of a method for determining the 3-dimensional structure of the catalytic domain of a gelatinase by X-ray crystallography.

In a preferred embodiment of the sixth aspect of the invention, the gelatinase is selected from the group consisting of 92 kDa gelatinase and 72 kDa gelatinase.

In a more preferred embodiment of the sixth aspect of the invention, the gelatinase is human gelatinase.

In a seventh aspect, the present invention consists of a method for structural determination by nuclear magnetic resonance spectroscopy of a gelatinase using isotope labeled human gelatinase catalytic domain protein wherein the label is $^{15}N$, $^{13}C$, and $^{2}H$.

As an active protein, the gelatinase catalytic domain protein will be useful in the treatment of various diseases. International Published Application WO 87/07907 discloses that mammalian stromelysin or prostromelysin is used in the debridement of dermal ulcers, modification of scar tissue formation arising from the healing of wounds such as burns and necrosis, and in the treatment of herniated vertebral discs.

Thus, in an eighth aspect, the present invention consists of a method of treating herniated vertebral discs comprising administering to a mammal suffering therefrom a therapeutically effective amount of the human gelatinase catalytic domain protein in unit dosage form.

In a ninth aspect, the present invention consists of a method of treating dermal ulcers comprising administering to a mammal suffering therefrom a therapeutically effective amount of the human gelatinase catalytic domain protein in unit dosage form.

In a tenth aspect, the present invention consists of a method of modifying scar tissue formation comprising administering to a mammal suffering therefrom a therapeutically effective amount of the human gelatinase catalytic domain protein in unit dosage form.

In an eleventh aspect, the present invention consists of a method of treating joint diseases amenable to treatment comprising administering to a mammal suffering therefrom a therapeutically effective amount of the human gelatinase catalytic domain protein in unit dosage form.

In a twelfth aspect, the present invention consists of a pharmaceutical composition adapted for administering a therapeutically effective amount of the human gelatinase catalytic domain protein in admixture with a pharmaceutically acceptable excipient, diluent, or carrier in the treatment methods mentioned above.

In a thirteenth aspect, the present invention consists of a method of using the human gelatinase catalytic domain protein to hydrolyze a protein substrate.

BRIEF DESCRIPTION OF THE DRAWINGS

The invention is further described by the following non-limiting examples which refer to the accompanying diagrams, FIGS. 1 to 7 and Tables 1 to 2, short particulars of which are given below.

FIGS. 1 and 1a (FIG. 1 shows a partial view of the amino acid sequence of GCD and FIG 1a is a continuation of FIG. 1 showing the remainder of the amino acid sequence) shows the amino acid sequence of GCD (Seq ID No: 1) and the sequence homology between GCD and SCD (Seq ID No: 2). Identical residues are indicated by colons. The secondary structures in SCD as determined by NMR (Van Doren S. R., et al., Biochemistry, 1993;32:13109–13122) are indicated by H (alpha-helix) and S (beta-sheet). The tryptophan (W104) in GCD connecting the two polypeptide fragments is underlined.

FIGS. 2, 2a and 2b (FIG. 2 shows a partial view of the nucleotide sequences of the synthetic gene for GCD, FIG. 2a is a continuation of FIG. 2 showing a partial view of the nucleotide sequence and FIG. 2b is a continuation of FIG. 2a showing the remainder of the nucleotide sequence) shows the nucleotide sequences of the synthetic gene for GCD (Seq ID No: 3). The oligonucleotides used in gene synthesis are underlined. The translated protein sequence and the restriction sites are indicated.

DETAILED DESCRIPTION OF THE INVENTION

Reconstruction of GCD

Matrix metalloproteinases are a family of homologous enzymes. The gelatinases are unique in that both 92 kDa and 72 kDa gelatinases have a fibronectin-like insert of approximately 19 kDa in the catalytic domain, separating the catalytic domain of gelatinases into two pieces. By sequence alignment among matrix metalloproteinases, we identified in human 72 kDa gelatinase (Collier I. E., et al., *J. Biol. Chem*, 1988;263:6579–6587) two tryptophan residues at the two junctions of the insert and connected the two pieces for the catalytic domain into a single polypeptide chain by merging the two tryptophans into one. The reconstructed GCD has 58% amino acid identity with SCD (FIG. 1), the C-terminally truncated stromelysin we expressed and characterized previously (Ye Q. -Z., et al., *Biochemistry*, 1992;31:11231–11235).

Expression and purification of GCD

The expression system utilizing T7 RNA polymerase (Studier F. W., et al., *Meth. Enzymol.*, 1990;185:60–89; Tabor S., et al., *Proc. Natl. Acad. Sci. USA*, 1985;82:1074–1078) was used for GCD expression in *E. coli*. The GCD synthetic gene replaced the NheI/HindIII fragment containing T7 gene 10 in the plasmid pGEMEX-1 (commercially available from Promega Corp., Madison, Wis.) and was situated behind a T7 promoter.

Figure 3:
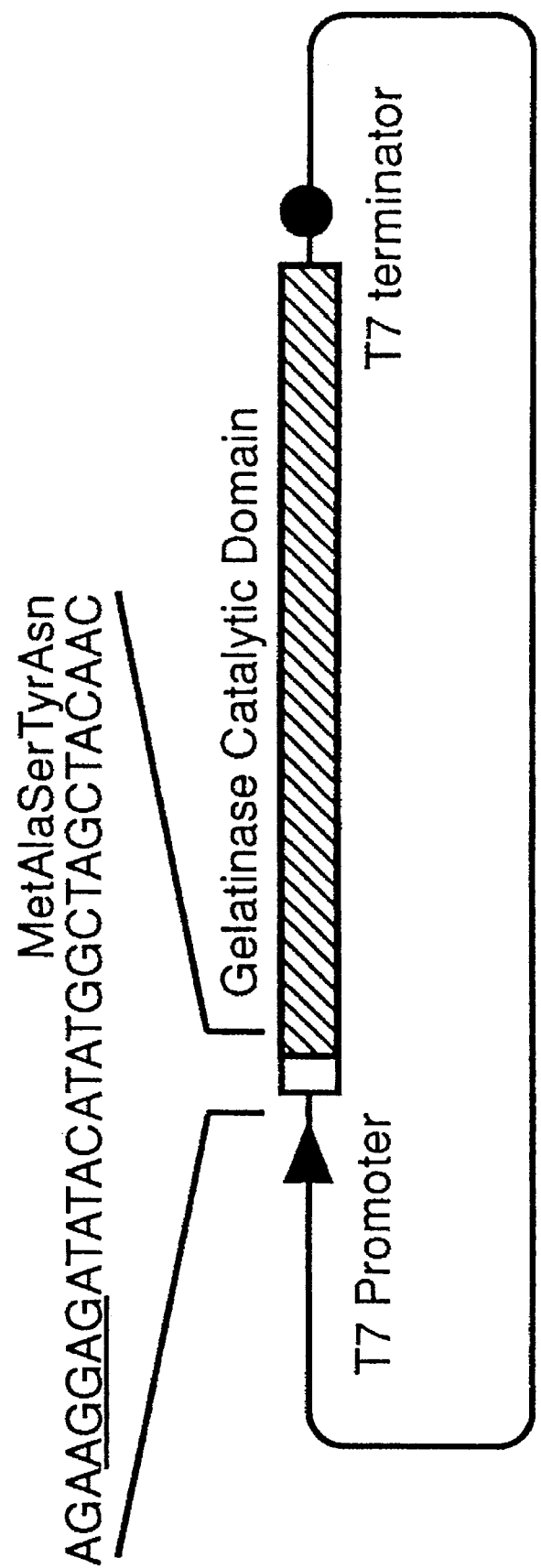
FIG. 3 shows the structure of the plasmid pGEMEX-GCD (3618 bases) for expressing GCD protein. Shown in detail is the sequence surrounding the N-terminus of the gene (Seq ID No: 4), where the ribosome binding site is underlined. Three amino acid residues (Met, Ala, and Ser) were added to the N-terminus of GCD protein as shown.
Figure 4:
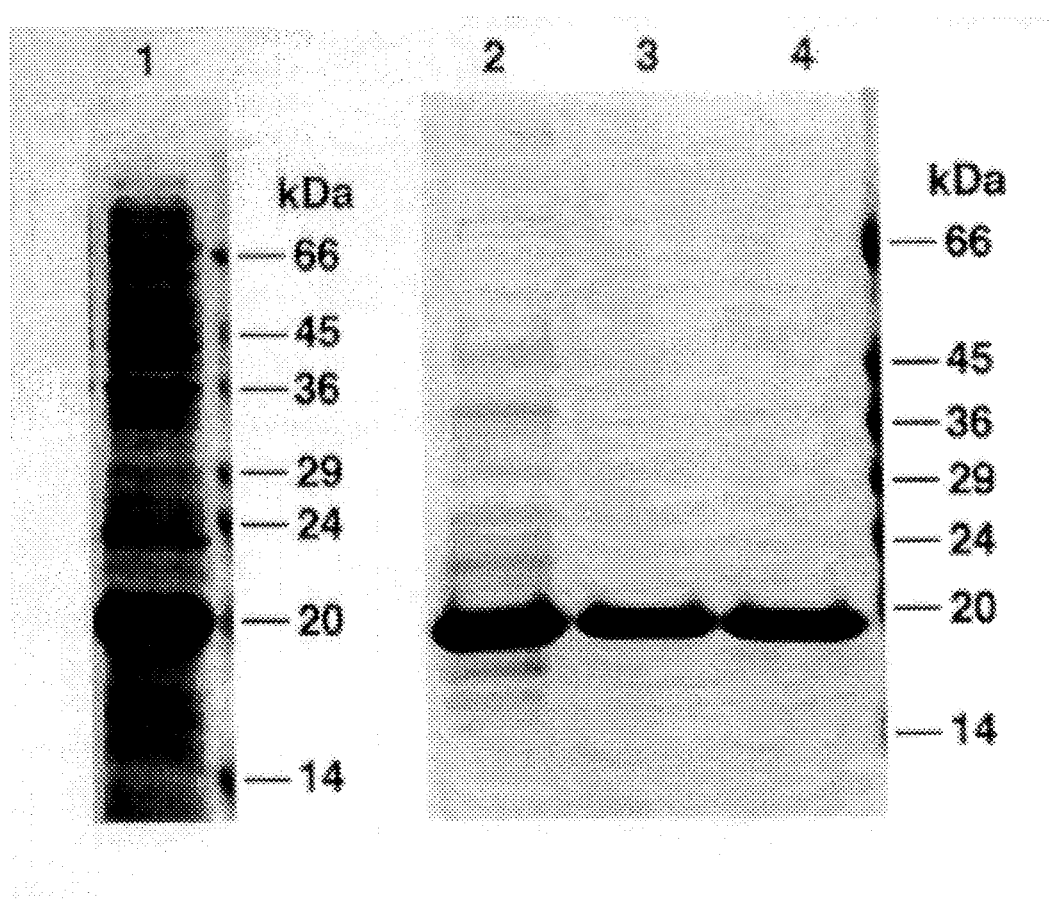
FIG. 4 shows the purification of GCD. The protein samples were analyzed by SDS-PAGE on 10–20% Tricine gel. Lane 1, E. coli cells before lysis; lane 2, GCD solution in Tris/urea before Q-Sepharose column; lane 3, combined active fractions after Q-Sepharose column; and lane 4, after dialysis against Tris buffer.

GCD was expressed in high yield as an insoluble protein, and its refolding in vitro was rapid and efficient both in the presence and in the absence of calcium and zinc ions. However, the refolding does not require either of the ions since GCD could refold in the presence of 1,10-phenanthroline or Chelex-100 resin (Bio-Rad). High yield of apo-enzyme was obtained after dialysis against 50 mM Tris·HCl at pH 7.6. The apo-enzyme was stable at 4° C. and showed instant activity when zinc and calcium were provided. The rapid refolding and instant activity makes it possible to monitor enzyme activity during purification even for column fractions containing 6M urea. The reconstruction of GCD gene left one cysteine residue in the protein molecule, and early attempts in GCD purification showed that the cysteine caused dimerization as analyzed by electrospray mass spectrometry. Since the cysteine is not present in other matrix metalloproteinases, iodoacetamide was used to block the cysteine thiol group before purification. After purification in the presence of 6M urea on Q-Sepharose column and subsequent dialysis, GCD was homogeneous when analyzed by reducing SDS-PAGE (FIG. 4).

The purified GCD was subjected to amino acid sequencing. The N-terminal sequence was determined as ASYNFF-PRKPKWDKNQITYRIIGYTPDLDP (Seq ID No: 6) as predicted from DNA sequence with methionine removed during *E. coli* expression. The molecular weight of 19,157 Da. as determined by electrospray mass spectrometry was consistent with a full length protein starting at Ala at position −2 and ending at Ile at 168 with $CH_2CONH_2$ group attached on the cysteine thiol (calculated molecular weight 19,154 Da.). The iodoacetamide modification was complete since no dimer or non-alkylated species was detectable by the electrospray mass spectrometry. The protein sample contained 0.34 atoms zinc per GCD molecule according to atomic absorption analysis.

pH Effect on GCD Activity

Figure 5:
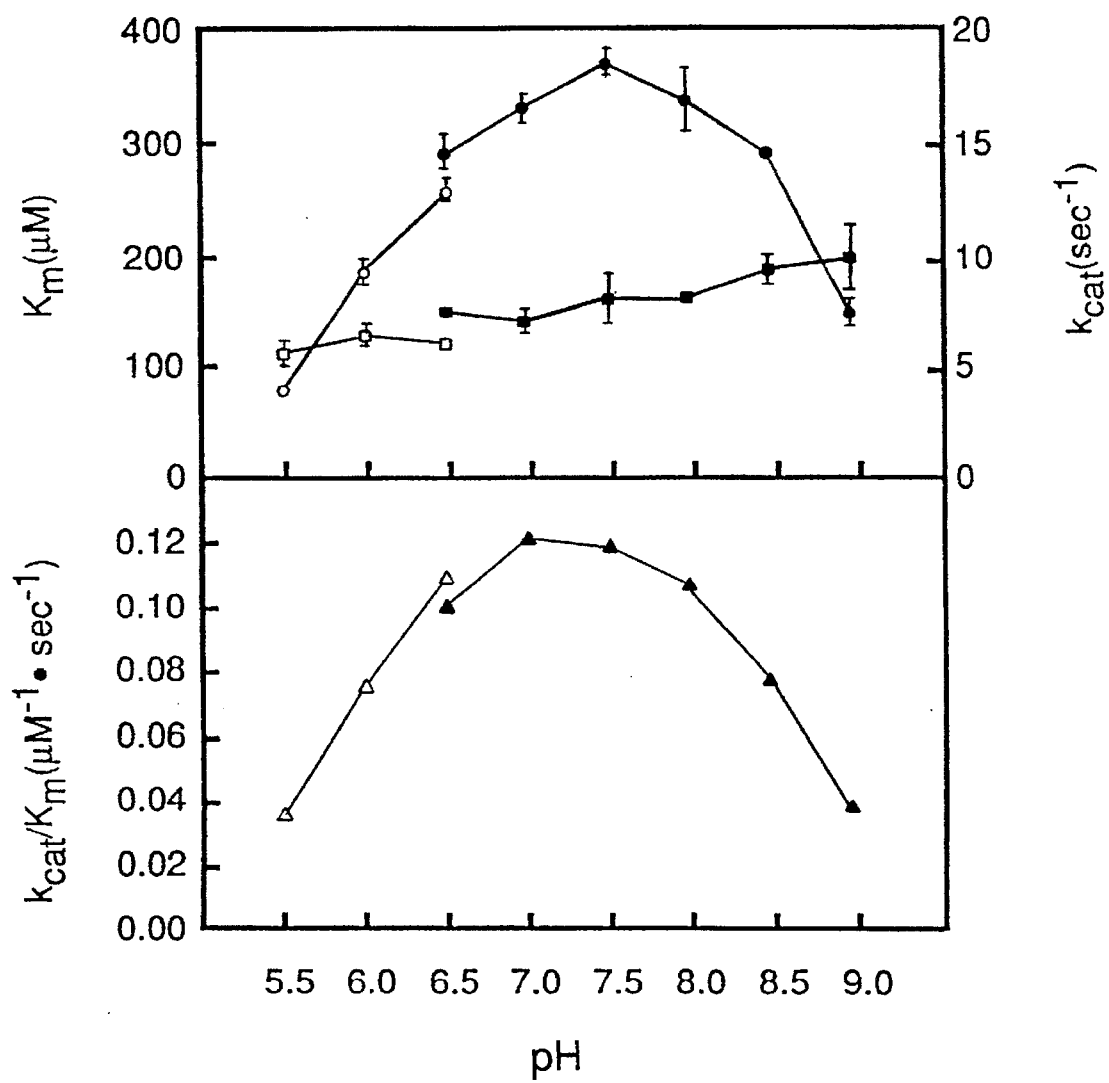
FIG. 5 shows pH effects on GCD activity. Hydrolysis of the thiopeptolide was monitored in MES buffer (pH 5.5 to 6.5, open circles, squares, and triangles) or Bis-Tris propane buffer (pH 6.5 to 9.0, closed circles, squares, and triangles). Values for $k_{cat}$ are shown as circles, those for $K_m$ are shown as squares, and those for $k_{cat}/K_m$ are shown as triangles.

We observed previously that SCD prefers slightly acidic condition for activity (Ye Q. -Z., et al., *Biochemistry*, 1992;31:11231–11235), which is consistent with the pH profile for full length stromelysin (Harrison R. K., et al., *Biochemistry*, 1992;31:10757–10762; Wilhelm S. M., et al., *J. Biol. Chem.*, 1993;268:21906–21913). For comparison, we tested GCD in hydrolyzing the thiopeptolide at pH range from 5.5 to 9.0 (FIG. 5). The $K_m$ for the thiopeptolide increased gradually with increasing pH (from 105 μM at pH 5.5 to 192 μM at pH 9.0), while $k_{cat}$ showed an optimum at pH 7.5 (18 $sec^{-1}$). The $k_{cat}/K_m$ had an optimum at pH 7.0 (0.119 $μM^{-1}·sec^{-1}$). The preference of GCD for expressing activity at neutral pH is consistent with the previous report that gelatinase is a neutral protease (Selzer J. L., et al., *J. Biol. Chem.*, 1981;256:4662–4668).

The Effect of Zinc and Calcium Concentrations on GCD Activity

Figure 6:
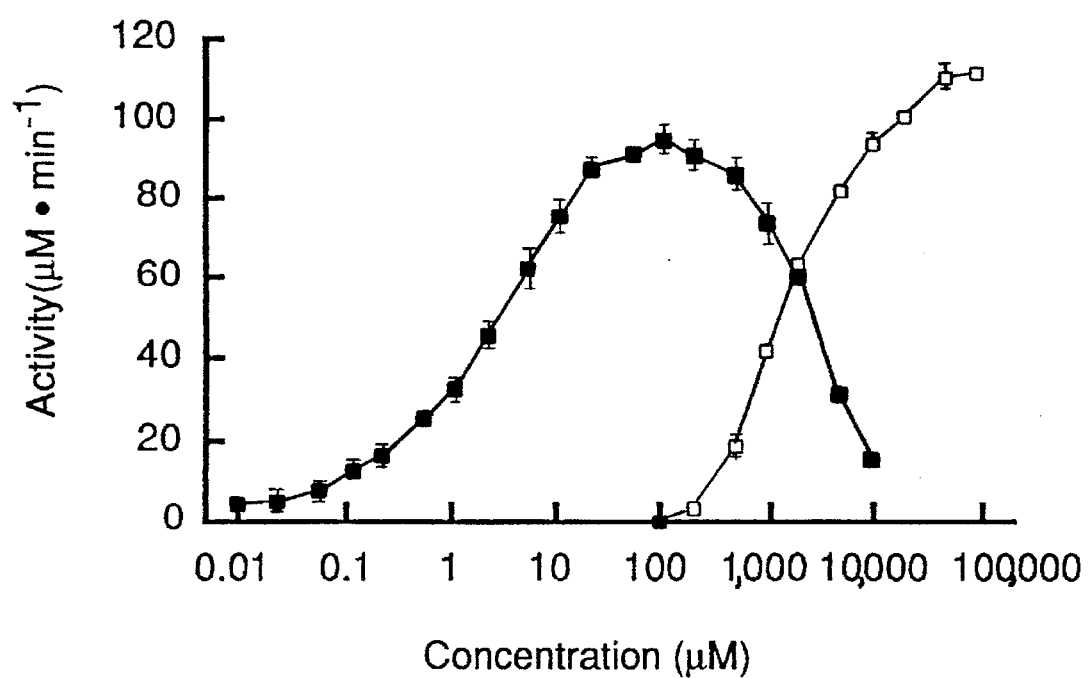
FIG. 6 shows the effects of zinc and calcium concentration on GCD activity. Hydrolysis of the thiopeptolide was monitored in MOPS buffer (pH 7.0). Activities at different $ZnCl_2$ concentration in the presence of 10 mM $CaCl_2$ are shown as closed squares, and activities at different $CaCl_2$ concentration in the presence of 100 µM $ZnCl_2$ are shown as open squares. GCD concentration at 173 nM is indicated by a vertical line.

The availability of apo-GCD offered an opportunity to study the structural and functional roles of zinc and calcium ions. We did not vigorously exclude metal ions during protein purification, so that it is not surprising to see a small amount of zinc (0.34 atoms per GCD molecule) in the GCD sample. Both calcium and zinc ions are required for activity, since either metal ion alone is not sufficient to restore GCD activity. In the presence of 10 mM $CaCl_2$, the optimal activity was achieved around 100 μM $ZnCl_2$ (FIG. 6), which is more than 500 equivalents of zinc with only 173 nM GCD present. This is in sharp contrast with C-terminally truncated stromelysin, for which only one equivalent of zinc was required for maximal activity (Salowe S. P., et al., *Biochemistry*, 1992;31:4535–4540). Higher zinc concentration (>100 μM) inhibited GCD activity. With 100 μM $ZnCl_2$ present in solution, GCD showed increased activity with the increase of calcium concentration up to 100 mM. The requirement for both zinc and calcium for activity explains the stability of GCD in Tris buffer without zinc or calcium, or with only one of the ions. Degradation occurred when GCD was incubated at 37° C. with both zinc and calcium present, and the degradation could be prevented by including GCD inhibitors.

Inhibition of GCD by SCD Inhibitors

We identified several amino acid derivatives as SCD inhibitors, and they also inhibited full length human stromelysin with the same potency rank order (Ye Q. -Z., et al., *J. Med. Chem.*, 1994;37:206–209). SCD and GCD share high sequence homology (FIG. 1), so that it was reasonable to test the SCD inhibitors on GCD. The benzyloxycarbonyl or the tert-butyloxycarbonyl moiety was required for GCD inhibition (Table 1), since L-tryptophan itself was not active. L-isomers of these amino acid derivatives always showed better inhibitory activity than the D-isomer. The closely related specificity for inhibitors displayed by GCD and SCD revealed the similarity as well as subtle differences at the active sites of GCD and SCD.

Comparison of Activity of GCD With Other Matrix Metalloproteinases

Figure 7:
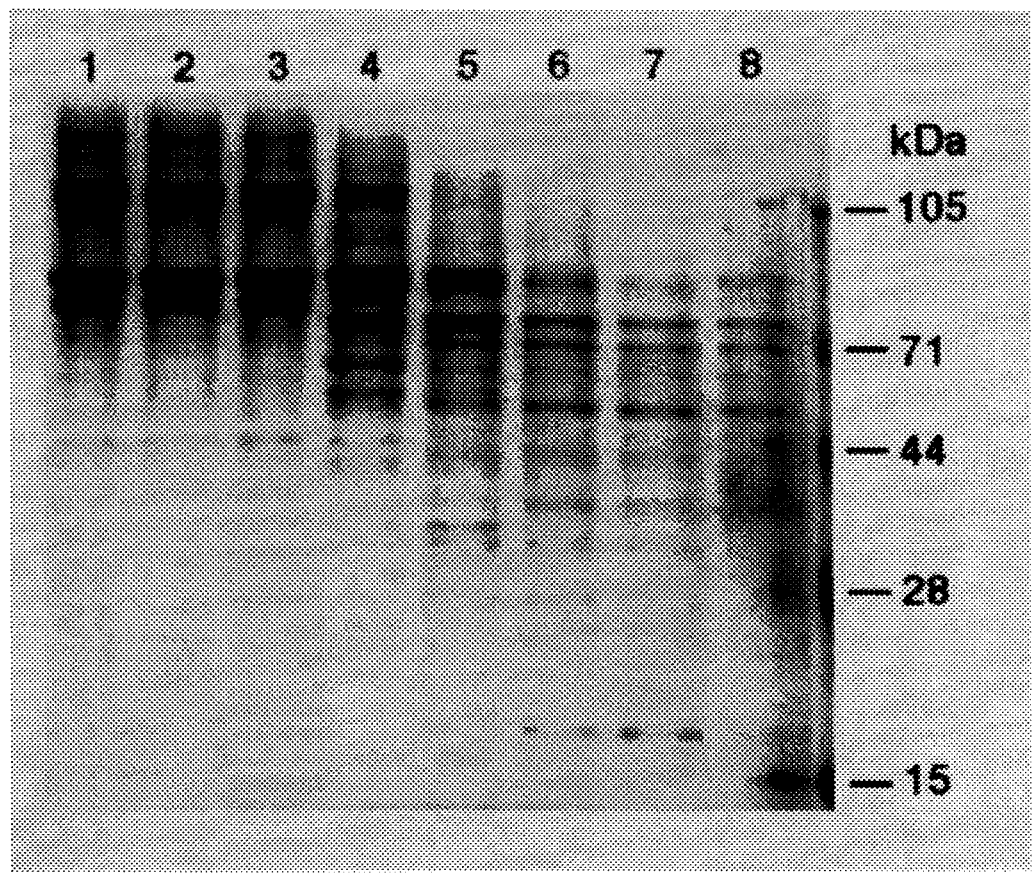
FIG. 7 shows the digestion of denatured Type I collagen (gelatin) by GCD. Protein samples were analyzed by SDS-PAGE on 10% Tris-glycine gel. Lane 1, gelatin (25 µg) alone at 0 minutes; lane 2, gelatin (25 µg) alone at 120 minutes; and lanes 3–8, gelatin (25 µg) with GCD (10 ng) at 0, 10, 30, 60, 90, and 120 minutes.

Both SCD and GCD cleave efficiently the fluorogenic peptides Mca-Pro-Leu-Gly-Leu-Dpa-Ala-Arg-$NH_2$ (Seq ID No: 7) and Dnp-Pro-Leu-Gly-Leu-Trp-Ala-D-Arg-$NH_2$ and the thiopeptolide Ac-Pro-Leu-Gly-thioester-Leu-Leu-Gly-OEt (Seq ID No: 8) (Table 2). GCD is approximately 10–20 times more active in the cleavages than SCD, which is consistent with previous reports that gelatinase is a more efficient enzyme in digesting synthetic substrates than stromelysin (Netzel-Arnett S., et al., *Anal. Biochem.*, 1991;195:86–92; Knight C. G., et al., *FEBS Lett.*, 1992;296:263–266). The efficiency in cleaving the fluorogenic peptides by GCD was close to the reported values for full length 72 kDa gelatinase (Knight C. G., et al., *FEBS Lett.*, 1992;296:263–266). GCD was capable of cleaving not only thiopeptolide and peptide substrates but also protein substrates such as gelatin (FIG. 7), the natural substrate for 72 kDa gelatinase.

TABLE 1

Inhibition of GCD and SCD by Amino Acid Derivatives

| | | GCD | | SCD[a] | |
|---|---|---|---|---|---|
| No. | Compound[b] | $IC_{50}$ (µM) | $K_i$ (µM) | $IC_{50}$ (µM) | $K_i$ (µM) |
| 1 | Cbz-L-Trp-OH | 6.1 ± 0.2 | 3.5 | 2.5 ± 0.9 | 2.1 |
| 2 | Cbz-D-Trp-OH | 128 ± 15 | 73 | 86 ± 34 | 71 |
| 3 | H-L-Trp-OH | >500 | | >500 | |
| 4 | H-D-Trp-OH | >500 | | >500 | |
| 5 | Boc-L-Trp-OH | 57 ± 4 | 33 | 10 ± 4 | 8 |
| 6 | Boc-D-Trp-OH | >500 | | 100–500 | |
| 7 | Cbz-L-Tyr-OH | 10.4 ± 0.4 | 6.0 | 24 ± 10 | 20 |
| 8 | Cbz-D-Tyr-OH | >500 | | 432 ± 215 | 356 |
| 9 | Cbz-L-Phe-OH | 21 ± 1 | 12 | 40 ± 8 | 33 |
| 10 | Cbz-D-Phe-OH | 100–500 | | >500 | |

[a]Data for SCD were taken from Ye Q.-Z., et al., J. Med, Chem., 1994;37:206–209.
[b]Abbreviations: Cbz, benzyloxycarbonyl, and Boc, tert-butyloxycarbonyl

TABLE 2

Catalytic Efficiency[a] in Cleaving Fluorogenic Peptides and Thiopeptolide by Matrix Metalloproteinases

| Enzyme | Mca/Dpa Peptide[b] | Dnp/Trp Peptide[b] | Thiopeptolide[b] |
|---|---|---|---|
| 72 kDa Gelatinase | 629,000[c] | 58,000[c] | |
| Stromelysin | 23,000[c] | 2,200[c] | |
| GCD | 184,000 | 112,000 | 119,400 |
| SCD | 10,000 | 13,700 | 7,840 |

[a]Catalytic efficiency was expressed as $k_{cat}/K_m$ ($M^{-1}sec^{-1}$).
[b]Mca/Dpa peptide, Mca-Pro-Leu-Gly-Leu-Dpa-Ala-Arg-NH₂ (Seq ID No: 7); Dnp/Trp peptide, Dnp-Pro-Leu-Gly-Leu-Trp-Ala-D-Arg-NH₂; and thiopeptolide, Ac-Pro-Leu-Gly-thioester-Leu-Leu-Gly-OEt (Seq ID No: 8).
[c]Values reported by Knight C. G., et al., FEBS Lett., 1992;296:263–266.

The GCD protein of the present invention is fully active as a proteinase and it is useful in mechanistic studies on catalysis and inhibition. Furthermore, the present invention discloses an efficient expression system and simple purification scheme for GCD protein. Additionally, the recombinant GCD protein can be obtained in large quantities.

Thus, GCD protein can be used to determine the 3-dimensional structure of the catalytic domain of a gelatinase by X-ray crystallography or nuclear magnetic resonance spectroscopy, which is carried out by methodology known in the art.

Also, GCD protein can be used in a screening assay to uncover inhibitors of a gelatinase which comprises mixing GCD protein with the candidate compound and determining the ability of GCD protein to cleave a substrate. Substrates such as, for example, gelatins, thiopeptolide, and the like may be used in the assay.

Additionally, GCD protein may be used to hydrolyze a protein substrate by methodology known in the art.

The protein of the present invention can be prepared and administered in a wide variety of oral and parenteral dosage forms. Thus, the protein of the present invention can be administered by injection, that is, intravenously, intramuscularly, intracutaneously, subcutaneously, intraduodenally, or intraperitoneally. Also, the protein of the present invention can be administered by inhalation, for example, intranasally. Additionally, the protein of the present invention can be administered transdermally. It will be obvious to those skilled in the art that the following dosage forms may comprise as the active component, either the protein or a corresponding pharmaceutically acceptable salt of the protein.

For preparing pharmaceutical compositions from the protein of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as an agent for treating herniated vertebral discs, dermal ulcers, modifying scar tissue formation, or joint diseases, the protein utilized in the pharmaceutical method of this invention is administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the protein being employed. Determination of the proper dosage for a particular situation is within the skill of the art. Generally, treatment is initiated with smaller dosages which are less than the optimum dose of the protein. Thereafter, the dosage is increased by small increments until the optimum effect under the circumstances is reached. For convenience, the total daily dosage may be divided and administered in portions during the day, if desired.

The following nonlimiting examples illustrate the inventor's preferred methods for preparing the protein of the invention.

MATERIALS AND METHODS

EXAMPLE 1

Gene Synthesis

The nature of the modification on the human 72 kDa gelatinase makes it more appealing to synthesize the GCD gene than to construct the gene from cDNA. The synthetic gene coding for the reconstituted GCD protein (FIG. 2) was assembled by a PCR-based gene synthesis method as described previously (Ye Q. -Z., et al., *Biochem. Biophys. Res. Commun.*, 1992;186:143–149). The sequences for the six long oligonucleotides (106mers) are shown in FIG. 2, and the two terminal oligonucleotides (20mers) have the sequences AACGAAAGTGCTAGCTACAA (Seq ID No: 9) and TGCATTGTTCAAGCTTAGAT (Seq ID No: 10). All oligonucleotides were synthesized on an ABI 394 DNA synthesizer using 40 nmol polystyrene columns and purified with the OPC cartridges (Applied Biosystems, Foster City, Calif.). The oligonucleotides were assembled to form a synthetic gene in a PCR reaction with 30 cycles at 94° C. for 1 minute, 55° C. for 2 minutes, and 72° C. for 3 minutes. Six long oligonucleotides (106mers) with 20 base overlapping sequences as the extension primers were assembled into a DNA fragment coding the GCD gene (Ho S. N., et al., *Gene*, 1989;77:51–59), and the DNA fragment was amplified by two terminal oligonucleotides (20mers). The PCR-generated DNA fragment was purified with GLASSMILK using the GENECLEAN II kit (BIO101, La Jolla, Calif.), digested with NheI and HindIII, and ligated to the plasmid pGEMEX-1 (Promega, Madison, Wis.) which had been digested with the same two restriction enzymes and dephosphorylated with calf intestine alkaline phosphatase. The recombinant plasmid pGEMEX-GCD was transformed into *E. coli* strain DH5α (BRL, Gaithersburg, Md.), and the sequence coding for the GCD gene was confirmed by DNA sequencing. In the synthetic gene, codons were optimized for *E. coli* expression, and restriction sites were introduced with even distribution for future mutagenesis studies. Extra codons for Met, Ala, and Ser were added to the N-terminus for translation initiation (Met) and restriction site NheI (Ala and Ser). The restriction site for HindIII was also added at the end of the gene after termination codon for cloning.

EXAMPLE 2

Expression and Purification

The pGEMEX-GCD plasmid was transformed into *E. coli* strain BL21(DE3)/pLysS cells (Novagen, Madison, Wis.) for expression. The transformed *E. coli* cells were cultured in 2×TY medium (16 g Tryptone, 10 g Yeast extract, and 5 g NaCl per liter) supplemented with carbenicillin (50 µg/mL) and chloramphenicol (50 µg/ml) at 37° C. in a two-liter table top fermenter to $OD_{600}$=1.7. GCD expression was induced by addition of isopropyl-β-D-thiogalactopyranoside (IPTG, 1 mM), and incubation continued for 3 hours at 37° C. The cells were harvested by centrifugation at 10,000 ×g for 10 minutes at 4° C. The cell pellet (8.3 g, wet weight) was washed once with 50 mM Tris·HCl (pH 7.6) and stored at −20° C. until use.

A portion of the cells (4.62 g cell paste, lane 1 in FIG. 4) was resuspended in 20 mL of 50 mM Tris·HCl (pH 7.6) containing 0.1% Triton X-100. After a few minutes, a small amount of DNase I and $MgCl_2$ (5 mM) were added to digest the released DNA. Pellets were collected after centrifugation, washed with water twice, and mixed with 3.6 g of urea (final concentration 6M) and water to a 10 mL final volume. The mixture was clarified by centrifugation and incubated at room temperature for 20 minutes after adding dithiothreitol (DTT) to 2 mM. Iodoacetamide (42 mg, final concentration 20 mM) was added to alkylate the cysteine's thiol group, and the mixture was incubated for 30 minutes at room temperature. DTT was added to 20 mM to inactivate residual iodoacetamide. The mixture was clarified by centrifugation, and a GCD solution was obtained (6.5 mL, 133 mg protein, lane 2 in FIG. 4).

The GCD solution was loaded to a Hi-Load Q-Sepharose column (20 mL, Pharmacia, Piscataway, N.J.) equilibrated previously with 50 mM Tris·HCl/6M urea (pH 7.6) and eluted with a linear NaCl gradient (0 to 1M) in the Tris/urea buffer. The combined active fractions (10 mL, 68 mg protein, lane 3 in FIG. 4) were dialyzed (membrane molecular weight cutoff 6–8 kDa) against 1 liter of 50 mM Tris·HCl (pH 7.6) overnight at 4° C. without stirring. The buffer was changed the next morning. The dialysate contained homogeneous GCD apo-protein (10.5 mL, 61 mg protein, lane 4 in FIG. 4). Reducing SDS-PAGE analysis was carried out on pre-cast 10–20% Tricine gels (NOVEX, San Diego, Calif.).

EXAMPLE 3

Cleavage of Thiopeptolide by GCD

The ability of GCD to cleave the thiopeptolide Ac-Pro-Leu-Gly-thioester-Leu-Leu-Gly-OEt (Seq ID No: 8) (Bachem Bioscience, King of Prussia, Pa.) was used to follow the enzymatic activity during purification and characterization as described previously for monitoring stromelysin catalytic domain (SCD) activity (Ye Q. -Z., et al., *Biochemistry*, 1992;31:11231–11235). The assays were carried out on 96 well plates with THERMOmax microplate reader (Molecular Devices, Menlo Park, Calif.) at room temperature (21°–22° C.), and OD changes at 405 nm in each wells were monitored continuously and simultaneously for 2 to 5 minutes. The 100 μL assay mixture typically contained 50 mM MOPS (pH 7.0), 1 mM DTNB, 100 μM thiopeptolide, 10 mM $CaCl_2$, 10 μM $ZnCl_2$, and the enzyme.

For determining activity at different pHs, 50 mM MES buffer was used for pH 5.5–6.5, and 50 mM Bis-Tris propane buffer was used for pH 6.5–9.0, in place of 50 mM MOPS buffer. Activities at pH 8.0, 8.5, and 9.0 were corrected for non-enzymatic degradation of the thiopeptolide. Substrate concentrations used range from 37–742 μM, GCD concentration was 173 nM, and values for $K_m$ and $V_{max}$ were obtained from non-linear regression of the plot of initial rates vs. substrate concentrations. The determinations were repeated three times. As a control, GCD was incubated in buffers at pH 5.5 to 9.0 for 5 minutes at room temperature, and then the activity was assayed at pH 7.0. Similar activity was observed for these samples, indicating that GCD was stable under the conditions for determining activity at pH 5.5 to 9.0.

The effects of zinc and calcium ion concentrations on GCD activity were investigated using 173 nM GCD in MOPS buffer at pH 7.0. In the presence of 10 mM $CaCl_2$, the GCD activity as the initial rate was determined with $ZnCl_2$ concentration ranging from 10 nM to 10 mM. In the presence of 100 μM $ZnCl_2$, the GCD activity was determined with $CaCl_2$ concentration ranging from 100 μM to 100 mM. The determinations were repeated at least three times.

The compounds tested for GCD inhibition were obtained from Bachem. Assays were performed with 17.3 nM GCD, 10 mM $CaCl_2$, and 10 μM $ZnCl_2$ in MOPS buffer at pH 7.0. Inhibition was initially tested at inhibitor concentrations of 100 and 500 μM. $IC_{50}$ values were determined when the compound showed 50% inhibition near or below 100 μM. $K_i$ values were derived from $IC_{50}$ values by using the equation $K_i=IC_{50}/(1+[substrate]/K_m)$ (Cheng Y. -C., et al., *Biochem. Pharmacol.*, 1973;22:3099–3108), where substrate concentration was 100 μM and $K_m$ for the substrate was 134 μM. The determinations were repeated three times.

EXAMPLE 4

Cleavage of Fluorogenic Peptides by GCD and SCD

The activity of GCD in comparison with SCD in cleaving peptides Mca-Pro-Leu-Gly-Leu-Dpa-Ala-Arg-$NH_2$ (Seq ID No: 7) and Dnp-Pro-Leu-Gly-Leu-Trp-Ala-D-Arg-$NH_2$ (both from Bachem) was assayed under the conditions described (Knight C. G., et al., *FEBS Lett.*, 1992;296:263–266) with minor modifications. The cleavage of the fluorogenic peptide Mca-Pro-Leu-Gly-Leu-Dpa-Ala-Arg-$NH_2$ (Seq ID No: 7) (1.6 and 4 μM) by GCD (10 nM) or SCD (100 nM) was monitored by measuring fluorescence at 393 nm with excitation at 328 nm at 25° C. continuously for 30 minutes in 50 mM MOPS buffer (pH 7.0) containing 10 mM $CaCl_2$ and 10 μM $ZnCl_2$. Similar conditions were used for peptide Dnp-Pro-Leu-Gly-Leu-Trp-Ala-D-Arg-$NH_2$ (7 and 10 μM) except excitation was at 283 nm and emission at 350 nm. The time course of the product generation was fitted exponentially as a first order reaction, to give $k_{app}$. The $k_{cat}/K_m$ value was derived from $k_{app}$ with the equation $k_{cat}/K_m=k_{app}/[E]$, where [E]=10 nM for GCD and 100 nM for SCD.

EXAMPLE 5

Digestion of Gelatin by GCD

Type I collagen from rat tail (Sigma, Saint Louis, Mo.) was denatured by heating at 95° C. for 10 minutes. Denatured Type I collagen (gelatin) was incubated with GCD at 37° C. in 50 mM MOPS buffer (pH 7.0) containing 10 mM $CaCl_2$ and 10 μM $ZnCl_2$. Aliquots were taken at 0, 10, 30, 60, 90, and 120 minutes and mixed with loading buffer and 2-mercaptoethanol for SDS-PAGE analysis on pre-cast 10% Tris-Glycine gels (NOVEX). The protein bands were visualized by Coomassie Blue staining. The GCD at the amount used was not visible by the staining. Under the same condition without GCD, the denatured Type I collagen showed no degradation during the 120 minutes incubation.

EXAMPLE 6

Determination of Protein Concentration

The Bradford method was used for determining protein concentration with the dye reagent from Bio-Rad (Hercules, Calif.) and BSA as the standard. The purified GCD concentration was also determined by measuring UV absorption at 205 nm with the same BSA as the standard and the filtrate from the GCD solution through ultrafiltration membrane (molecular weight cutoff 5 kDa) as the blank. The ratio of the GCD protein concentrations determined by using the Bio-Rad reagent and by $OD_{205}$ was 1:1.18.

---

We claim:

1. A process for the production of the catalytic domain, without propeptide, C-terminal domain, and fibronectin-like insert, of human 72 kDa gelatinase having SEQ ID NO: 1 comprising culturing an E. coli host cell transformed with a replicable expression vector which expresses recombinant human 72 kDa gelatinase catalytic domain protein.

2. A process according to claim 1 wherein the expression of human gelatinase catalytic domain protein is under the control of bacterial phage T7 promoter.

3. A process according to claim 1 wherein the expression of human gelatinase catalytic domain protein is under the control of a non-T7 promoter selected from the group consisting of: a phage T3 promoter; a phage SP6 promoter; E. coli tac promoter; E. coli trc promoter; E. coli trp promoter; E. coli lac promoter; a phage lambda-$P_L$ promoter; and a phage lambda-$P_R$ promoter.

4. A process according to claim 1 wherein the expression vector is pGEMEX-GCD comprising the GCD synthetic gene of Seq ID No: 3 inserted into the plasmid pGEMEX-1.

5. A plasmid pGEMEX-GCD capable of expressing gelatinase catalytic domain protein which is constructed by inserting a synthetic DNA fragment of Seq ID No: 3 coding for the protein into plasmid pGEMEX-1.

6. A synthetic gene having Seq ID No: 3 coding for the human gelatinase catalytic domain.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 171 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Met Ala Ser Tyr Asn Phe Phe Pro Arg Lys Pro Lys Trp Asp Lys Asn
-3      -1   1              5                    10
Gln Ile Thr Tyr Arg Ile Ile Gly Tyr Thr Pro Asp Leu Asp Pro Glu
    15              20                  25
Thr Val Asp Asp Ala Phe Ala Arg Ala Phe Gln Val Trp Ser Asp Val
30              35                  40                      45
Thr Pro Leu Arg Phe Ser Arg Ile His Asp Gly Glu Ala Asp Ile Met
            50                  55                      60
Ile Asn Phe Gly Arg Trp Glu His Gly Asp Gly Tyr Pro Phe Asp Gly
            65                  70                  75
Lys Asp Gly Leu Leu Ala His Ala Phe Ala Pro Gly Thr Gly Val Gly
        80                  85                  90
Gly Asp Ser His Phe Asp Asp Glu Leu Trp Gly Phe Cys Pro Asp
    95              100                 105                 110
Gln Gly Tyr Ser Leu Phe Leu Val Ala Ala His Glu Phe Gly His Ala
                115                 120                 125
Met Gly Leu Glu His Ser Gln Asp Pro Gly Ala Leu Met Ala Pro Ile
            130                 135                 140
Tyr Thr Tyr Thr Lys Asn Phe Arg Leu Ser Gln Asp Asp Ile Lys Gly
            145                 150                 155
Ile Gln Glu Leu Tyr Gly Ala Ser Pro Asp Ile
    160                 165             169

(2) INFORMATION FOR SEQ ID NO:2:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Phe Arg Thr Phe Pro Gly Ile Pro Lys Trp Arg Lys Thr His Leu Thr
1               5                   10                  15
Tyr Arg Ile Val Asn Tyr Thr Pro Asp Leu Pro Lys Asp Ala Val Asp
            20                  25                  30
Ser Ala Val Glu Lys Ala Leu Lys Val Trp Glu Glu Val Thr Pro Leu
        35                  40                  45
Thr Phe Ser Arg Leu Tyr Glu Gly Glu Ala Asp Ile Met Ile Ser Phe
    50                  55                  60
Ala Val Arg Glu His Gly Asp Phe Tyr Pro Phe Asp Gly Pro Gly Asn
65                  70                  75                  80
Val Leu Ala His Ala Tyr Ala Pro Gly Pro Gly Ile Asn Gly Asp Ala
            85                  90                  95
His Phe Asp Asp Asp Glu Gln Trp Thr Lys Asp Thr Thr Gly Thr Asn
                100                 105                 110
Leu Phe Leu Val Ala Ala His Glu Ile Gly His Ser Leu Gly Leu Phe
            115                 120                 125
His Ser Ala Asn Thr Glu Ala Leu Met Tyr Pro Leu Tyr His Ser Leu
    130                 135                 140
Thr Asp Leu Thr Arg Phe Arg Leu Ser Gln Asp Asp Ile Asn Gly Ile
145                 150                 155                 160
Gln Ser Leu Tyr Gly Pro Pro Pro Asp Ser Pro Glu Thr Pro
                165                 170

( 2 ) INFORMATION FOR SEQ ID NO:3:

( i ) SEQUENCE CHARACTERISTICS:
        ( A ) LENGTH: 536 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

```
AACGAAAGTG CTAGCTACAA CTTCTTCCCG CGTAAACCGA AGTGGGACAA AAACCAGATC      60
ACTTACCGTA TCATCGGTTA CACCCCGGAC CTGGATCCGG AAACTGTAGA CGATGCATTC     120
GCACGTGCAT TCCAGGTGTG GTCTGACGTT ACTCCGCTGC GTTTCTCTCG CATCCATGAC     180
GGTGAAGCAG ACATCATGAT AAACTTCGGT CGTTGGGAAC ATGGTGACGG CTACCCGTTT     240
GATGGTAAAG ACGGTCTGCT GGCACATGCC TTCGCTCCGG GTACCGGTGT TGGTGGTGAC     300
TCTCACTTCG ACGATGATGA GCTGTGGGGT TTCTGCCCGG ATCAGGGCTA CTCTCTGTTC     360
CTGGTAGCTG CTCACGAATT CGGTCATGCT ATGGGTCTGG AGCACTCCCA GGACCCGGGT     420
GCTCTGATGG CTCCGATATA CACCTATACT AAAAACTTTC GTCTGTCCCA GGACGATATC     480
AAAGGTATAC AGGAACTGTA CGGTGCTTCT CCGGACATCT AAGCTTGAAC AATGCA         536
```

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (synthetic)

( x i ) SEQUENCE DESCRIPTION: SEQ ID NO:4:

```
AGAAGGAGAT ATACATATGG CTAGCTACAA C                                     31
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Met Ala Ser Tyr Asn
1               5
```

( 2 ) INFORMATION FOR SEQ ID NO:6:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ala Ser Tyr Asn Phe Phe Pro Arg Lys Pro Lys Trp Asp Lys Asn Gln
-2  -1  1               5                   10
Ile Thr Tyr Arg Ile Ile Gly Tyr Thr Pro Asp Leu Asp Pro
15                  20                  25
```

( 2 ) INFORMATION FOR SEQ ID NO:7:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:7:

Pro Leu Gly Leu Xaa Ala Arg
1               5

( 2 ) INFORMATION FOR SEQ ID NO:8:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Thiolester-bond
      ( B ) LOCATION: 3..4

( x i ) SEQUENCE DESCRIPTION: SEQ ID NO:8:

Pro Leu Gly Leu Leu Gly
1               5

( 2 ) INFORMATION FOR SEQ ID NO:9:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:9:

AACGAAAGTG CTAGCTACAA                                                              20

( 2 ) INFORMATION FOR SEQ ID NO:10:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:10:

TGCATTGTTC AAGCTTAGAT                                                              20